(12) United States Patent
Giordano et al.

(10) Patent No.: US 8,124,787 B2
(45) Date of Patent: Feb. 28, 2012

(54) PROCESS FOR THE PRODUCTION OF PYRAZOLES

(75) Inventors: Fanny Giordano, Muenchwilen (CH); Thomas Vettiger, Muenchwilen (CH); Juerg Gustav Wiss, Muenchwilen (CH); Linhua Wang, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 162 days.

(21) Appl. No.: 12/601,647

(22) PCT Filed: May 13, 2008

(86) PCT No.: PCT/EP2008/003841
§ 371 (c)(1),
(2), (4) Date: Nov. 24, 2009

(87) PCT Pub. No.: WO2008/145257
PCT Pub. Date: Dec. 4, 2008

(65) Prior Publication Data
US 2010/0174093 A1   Jul. 8, 2010

(30) Foreign Application Priority Data

May 31, 2007  (EP) .................................... 07010770
Sep. 26, 2007  (GB) .................................. 0718787.5

(51) Int. Cl.
*C07D 231/10*   (2006.01)
(52) U.S. Cl. .................................................. 548/374.1
(58) Field of Classification Search ................ 548/374.1
See application file for complete search history.

(56) References Cited

U.S. PATENT DOCUMENTS

| 5,498,624 A | 3/1996 | McLoughlin et al. |
| 2008/0108686 A1 | 5/2008 | Gewehr et al. |
| 2008/0154045 A1 | 6/2008 | Aihara et al. |

FOREIGN PATENT DOCUMENTS

| JP | 2002128763 | | 5/2002 |
| WO | 2005003077 | A | 1/2005 |
| WO | 2005042468 | A | 5/2005 |
| WO | 2005123690 | A | 12/2005 |
| WO | 2006090778 | A | 8/2006 |

OTHER PUBLICATIONS

"CRC Handbook of Chemistry and Physics, 76th Edition" 1995, CRC Press, Boca Raton, US, p. 3-1; p. 3-144, compound No. 5187; p. 3-246, compound No. 8981. The Fifth Series of Experimental Chemistry, vol. 16, "Synthesis of Organic Compounds IV", Mar. 31, 2007.

*Primary Examiner* — Rebecca Anderson
*Assistant Examiner* — Samantha Shterengarts
(74) *Attorney, Agent, or Firm* — R. Kody Jones

(57) ABSTRACT

A process for the production of a compound of formula (I), which comprises a) reacting a compound of formula (II), wherein $R_1$ and $R_2$ are both independently $C_1$-$C_6$ alkyl, with methylhydrazine in the presence of water and a water-immiscible organic solvent being inert in saponification reactions, to form a compound of formula (III) wherein $R_1$ is as defined for formula (II) and b) saponifying that compound in situ leading to the formation of the compound of formula (I) by b1) adding a base to form the anion of the compound of formula (I) and then adding an; acid to form the compound of formula (I); or b2) adding an acid to form the compound of formula (I).

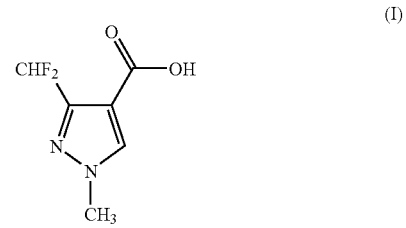

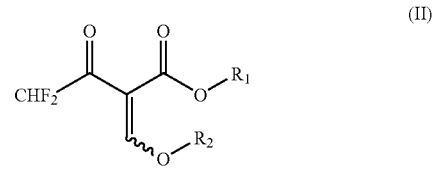

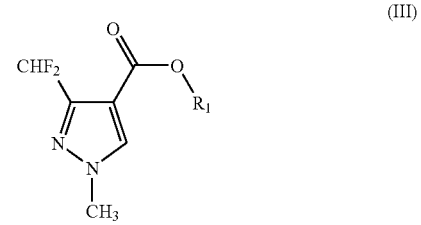

22 Claims, No Drawings

PROCESS FOR THE PRODUCTION OF PYRAZOLES

This application is a 371 of International Application No. PCT/EP2008/003841 filed May 13, 2008, which claims priority to EP 07010770.1 filed May 31, 2007, and GB 0718787.5 filed Sep. 26, 2007, the contents of which are incorporated herein by reference.

The present invention relates to a process for the production of 3-difluoromethyl-1-methyl-1H-pyrazole-4-carboxylic acid, which is useful as intermediate in fungicide production.

Said 3-difluoromethyl-1-methyl-1H-pyrazole-4-carboxylic acid (compound of formula I) can be used for the production of fungicides, which are described, for example, in WO 03/74491, WO 04/35589, WO 03/70705, WO 07/17450, WO 06/120219 and WO 06/87343.

Fungicides are generally produced in large quantities. For example, the fungicide chlorothalonil has been produced in the year 2005 in a quantity of over 23,000 metric tons.

The aim of the present invention is therefore to provide a novel process for the production of 3-difluoromethyl-1-methyl-1H-pyrazole-4-carboxylic acid that makes it possible to prepare said compound with high regioselectivity (in respect to the two isomers 3-difluoromethyl- and 5-difluoromethyl-1-methyl-1H-pyrazole-4-carboxylic acid), in high yields and good quality in an economically advantageous and easily handled way.

The present invention accordingly relates to a process for the production of a compound of formula I

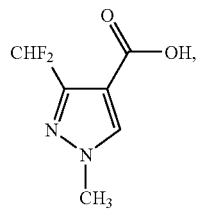

which comprises
a) reacting a compound of formula II

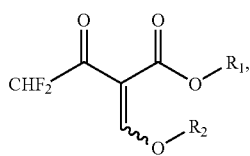

wherein $R_1$ and $R_2$ are both independently $C_1$-$C_6$alkyl, with methylhydrazine in the presence of water and a water-immiscible organic solvent being inert in saponification reactions, to form a compound of formula III

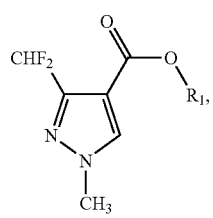

wherein $R_1$ is as defined for formula I; and
b) saponifying that compound in situ leading to the formation of the compound of formula I by
b1) adding a base to form the anion of the compound of formula I and then adding an acid to form the compound of formula I; or
b2) adding an acid to form the compound of formula I.

A process for making the intermediate compound of formula III is known from WO06/090778.

The invention further provides an improved process for process step a) i.e. the preparation of the intermediate compound of formula III. Accordingly there is provided a process for the production of a compound of formula III

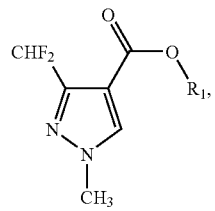

wherein $R_1$ is $C_1$-$C_6$alkyl which comprises reacting a compound of formula II

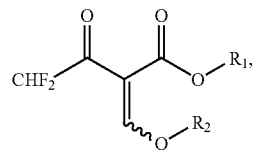

wherein $R_1$ and $R_2$ are both independently $C_1$-$C_6$alkyl, with methylhydrazine in the presence of water and a water-immiscible organic solvent in the absence of a base.

The alkyl groups appearing in the above substituent definitions may be straight-chain or branched and are, for example, methyl, ethyl, n-propyl, isopropyl, n-butyl, sec-butyl, isobutyl or tert-butyl, preferably methyl or ethyl.

Compounds of formula II occur in two isomers with regard to the double bond substituted by the alkoxy group —O—$R_2$: the E- and the Z-isomer. Both isomers or mixtures thereof can be used in the processes according to the invention.

In preferred processes, methylhydrazine is reacted in process step a) with compounds of formula II wherein $R_1$ and $R_2$ are both ethyl.

Process Step a):

In step a), methylhydrazine can be used in equimolar amounts, in sub-equimolar amounts or in excess relative to compounds of formula II, preferably methylhydrazine is used in equimolar amounts. Thus the molar ratio of methyl hydrazine:compound of formula II is preferably from 1:0.8 to 1:1.2.

In one embodiment of the invention, methylhydrazine is used in the form of an aqueous solution, such as a 35% (w/w) or 40% (w/w) aqueous solution.

The organic solvent used in step a) is inert in saponification reactions as said solvent is present also in the saponification step b).

The organic solvent used in step a) is water-immiscible. According to the invention "water-immiscible" means that when the organic solvent is mixed with water under the conditions of the process according to the invention two separate liquid phases are formed.

Preferred organic solvents are optionally halogenated aromatic hydrocarbon solvents, ketone solvents, optionally halogenated hydrocarbon solvents or ether solvents. In said definitions, halogen is generally fluorine, chlorine, bromine and/or iodine, preferably fluorine, bromine and/or chlorine.

Preferred "optionally halogenated aromatic hydrocarbon solvents" are benzene, toluene, xylene, chlorobenzene and dichlorobenzene; more preferred are toluene and xylene; most preferred is xylene.

Preferred "ketone solvent" is methylisobutylketone. Preferred "optionally halogenated hydrocarbon solvents" are pentane, hexane, octane, cyclohexane, chloroform and carbon tetrachloride; more preferred is cyclohexane. Preferred "ether solvent" is dioxane.

Preferred organic solvents are optionally halogenated aromatic hydrocarbon solvents and/or
ketone solvents; more preferred are aromatic hydrocarbon solvents and/or ketone solvents. In one embodiment of the invention, the organic solvent is an aromatic hydrocarbon solvent, especially xylene. In one embodiment of the invention, the organic solvent is methylisobutylketone.

The compounds of formula II are known or can be prepared analogously to processes known in the literature. For example, such compounds can be prepared from the 3-oxo-carboxylic acid esters on which they are based as described in WO 93/11117.

Process step a) is preferably carried out in a temperature range of from −20° C. to 50° C., preferably from 0° C. to 50° C., especially from 10° C. to 25° C.

The reaction time for process step a) is generally from 15 minutes to 48 hours, preferably 15 minutes to 18 hours, more preferably 15 minutes to 5 hours or from 1 to 5 hours. Said step can be carried out at normal, elevated or reduced pressure. In one embodiment, said step is carried out at normal pressure.

In one embodiment a base is used in process step a). The base is preferably selected from inorganic bases, such as hydroxides, for example LiOH, NaOH or KOH. Bases to which preference is given are hydroxides, such as NaOH or KOH; especially preferred is NaOH.

When a base is used in step a) preferably at least one equivalent of water is added at the start of the reaction relative to compounds of formula II; more preferably at least 10 equivalents of water are added, more preferably from 10 to 30 equivalents of water are added.

When a base is used in process step a) the molar ratio between water added at the start of the reaction and the organic solvent is preferably from 20:1 to 1:20; more preferably from 10:1 to 1:10. In one embodiment said molar ratio is from 10:1 to 1:1. This molar ratio according to the invention does not include the water being formed by the consumption of compounds of formula II by the condensation reaction of step a). Maximally one equivalent of water relative to compounds of formula II can be formed An example of performing step a) using a base comprises:
preparing an aqueous solution comprising methylhydrazine and the base,
preparing a solution of the compound of formula II in the organic solvent, and
mixing both solutions.

In said embodiment, the aqueous solution comprising methylhydrazine and the base can be added to the solution of the compound of formula II in the organic solvent or vice versa. In one embodiment, the solution of the compound of formula II in the organic solvent is added to the aqueous solution comprising methylhydrazine and the base. Preferably the base is present in step a) in an amount of 0.1 to 0.5 equivalents relative to the compounds of formula II used.

In another preferred embodiment process a) is performed without the addition of a base. In this embodiment it is preferred to have a molar ratio of methylhydrazine:compound of formula II of from 1:0.8 to 1:1.2, preferably 1:1. The molar ratio of methylhydrazine to organic solvent is preferably from 1:1 to 1:20, more preferably 1:1 to 1:5, even more preferably from 1:1 to 1:2. The mass ratio of methylhydrazine 35% to organic solvent is preferably from 1:1 to 1:20, more preferably 1:1 to 1:5, even more preferably from 1:1 to 1:1.5. The molar ratio of compound of formula II to organic solvent is preferably from 1:1 to 1:20, more preferably 1:1 to 1:5, even more preferably from 1:2 to 1:4. The mass ratio of compound of formula II to organic solvent is preferably from 1:1 to 1:20, more preferably 1:1 to 1:5, even more preferably from 1:1 to 1:2.

In this embodiment it is preferred to perform the process at −20° C. to 50° C., preferably from 0° C. to 50° C., more preferably from 0° C. to 25° C. and especially 10-25° C.

When no base is used in step a) it is not essential to add any extra water if an aqueous solution of methylhydrazine such as a 35% (w/w) or 40% (w/w) aqueous solution is used. However if 40% w/w methylhydrazine is used as a starting material it is preferred to add sufficient water to dilute the methyl hydrazine to 35% w/w.

An example of a step a) according to this embodiment is a process step comprising:
preparing a solution comprising methylhydrazine in water and the organic solvent,
preparing a solution of the compound of formula II in the organic solvent, and
mixing both solutions.

In said embodiment, the solution comprising methylhydrazine can be added to the solution of the compound of formula II in the organic solvent or vice versa. In one embodiment, the solution of the compound of formula II in the organic solvent is added to the solution comprising methylhydrazine.

Process Step b):

Step b), the saponification, is carried out directly after step a) without isolation of compounds of formula II (the compounds of formula II are used in situ). This is an important advantage of the process according to the invention, which leads to significant cost savings taken especially into account the large-scale production of fungicides. According to the invention, step b) can be carried out as described under step b1) (alkaline saponification) or under step b2) (acidic saponification).

Process Step b1):

Step b1) can be divided into two sub-steps: i) the formation of the anion of the compound of formula I ("the anion") by adding a base and ii) the formation of the compound of formula I ("the free acid") by later adding an acid.

The base is preferably selected from inorganic bases, such as hydroxides, for example LiOH, NaOH or KOH. Bases to which preference is given are hydroxides, such as NaOH or KOH; especially preferred is NaOH.

A suitable amount of base for anion formation is, for example, at least one equivalent relative to compounds of formula II used in step a), preferably from 1 to 5 equivalents; more preferably from 1 to 3 equivalents.

The formation of the anion is preferably carried out in a temperature range of from 40° C. to 100° C., especially from 40° C. to 70° C. The reaction time for anion formation is generally from 15 minutes to 48 hours, preferably from 15 minutes to 18 hours, more preferably 15 minutes to 5 hours or 1 to 5 hours. Said anion formation can be carried out at normal, elevated or reduced pressure, preferably at normal pressure.

In one embodiment of the invention, a base is already present in step a). Said base is typically the same as used later for anion formation in step b1) and is preferably a hydroxide, such as NaOH or KOH (especially preferably NaOH). An example of a step a) according to this embodiment is a process step comprising:
preparing an aqueous solution comprising methylhydrazine and the base,
preparing a solution of the compound of formula II in the organic solvent, and
mixing both solutions.

In said embodiment, the aqueous solution comprising methylhydrazine and the base can be added to the solution of the compound of formula II in the organic solvent or vice versa. In one embodiment, the solution of the compound of formula II in the organic solvent is added to the aqueous solution comprising methylhydrazine and the base.

Preferably the base is present in step a) in an amount of 0.1 to 0.5 equivalents relative to the compounds of formula II used and further base is added for anion formation so that a total amount of base is then present of at least 1 equivalent relative to the amount of compounds of formula II, preferably from 1 to 5 equivalents; more preferably from 1 to 3 equivalents. In one embodiment, about 0.2 equivalents relative to the compounds of formula II are present in step a).

After formation of the anion, said anion is typically present in the aqueous phase of the reaction mixture. In a preferred embodiment of the invention, the aqueous phase is isolated from the organic phase before the acid is added.

In one embodiment of the invention, the acid is added leading to an adjustment of the pH of the aqueous phase to a value of 7 or below, preferably 6 or below, more preferably 5 or below.

Suitable acids are inorganic acids, such as hydrochloric acid or sulfuric acid; or organic acids, such as formic acid, acetic acid or propionic acid. Preference is given to inorganic acids and special preference is given to hydrochloric acid.

The acid is added preferably in a temperature range of from 50° C. to 95° C., especially from 80° C. to 95° C.

The reaction time for formation of the free acid is generally from 15 minutes to 48 hours, preferably from 15 minutes to 18 hours, more preferably 15 minutes to 5 hours or from 1 to 5 hours. Said free acid formation can be carried out at normal, elevated or reduced pressure, preferably at normal pressure.

In another important embodiment of the invention, no base is used in step a) and the base must be added to perform step b1). The base is preferably a hydroxide, such as NaOH or KOH (especially preferably NaOH). An example of a step a) according to this embodiment is a process step comprising:
preparing a solution comprising methylhydrazine in water and the organic solvent,
preparing a solution of the compound of formula II in the organic solvent, and
mixing both solutions.

In said embodiment, the solution comprising methylhydrazine can be added to the solution of the compound of formula II in the organic solvent or vice versa. In one embodiment, the solution of the compound of formula II in the organic solvent is added to the solution comprising methylhydrazine.

Base is added for anion formation so that the amount of base is present of at least 1 equivalent relative to the amount of compounds of formula II, preferably from 1 to 5 equivalents; more preferably from 1 to 3 equivalents.

After formation of the anion, said anion is typically present in the aqueous phase of the reaction mixture. In a preferred embodiment of the invention, the aqueous phase is isolated from the organic phase before the acid is added.

In one embodiment of the invention, the acid is added leading to an adjustment of the pH of the aqueous phase to a value of 7 or below, preferably 6 or below, more preferably 5 or below.

Suitable acids are inorganic acids, such as hydrochloric acid or sulfuric acid; or organic acids, such as formic acid, acetic acid or propionic acid. Preference is given to inorganic acids and special preference is given to hydrochloric acid.

The acid is added preferably in a temperature range of from 50° C. to 95° C., especially from 80° C. to 95° C.

The reaction time for formation of the free acid is generally from 15 minutes to 48 hours, preferably from 15 minutes to 18 hours, more preferably 15 minutes to 5 hours or from 1 to 5 hours. Said free acid formation can be carried out at normal, elevated or reduced pressure, preferably at normal pressure.

Process Step b2):

In process step b2) the compound of formula I ("the free acid") is formed directly by acidic saponification.

The acid used in step b2) is typically an inorganic acid, such as hydrochloric acid or sulfuric acid; or an organic acid, such as formic acid, acetic acid or propionic acid. Preference is given to inorganic acids and special preference is given to hydrochloric acid.

A preferable amount of acid is at least 0.01 equivalents relative to compounds of formula II used in step a), more preferably from 0.01 to 5 equivalents; even more preferably from 1 to 5 equivalents, most preferably from 1 to 3 equivalents.

The formation of the free acid is preferably carried out in a temperature range of from 40° C. to 100° C., especially from 40° C. to 60° C. The reaction time is generally from 15 minutes to 48 hours, preferably from 15 minutes to 18 hours, more preferably 15 minutes to 5 hours or 1 to 5 hours. Said free acid formation can be carried out at normal, elevated or reduced pressure, preferably at normal pressure.

As the compound of formula II typically is present in the organic phase after step a), in a preferred embodiment of the invention, the organic phase is isolated from the aqueous phase before the acid is added in step b2).

Isolation of Compound of Formula I After Performing Process Step b1) or b2):

Under typical process conditions described above, the compounds of formula I precipitate and can be easily isolated after performing process steps b1) or b2). Typically this is done by cooling followed by filtration.

The present invention makes it possible to produce compounds of formula I in a high yield, with a high degree of regioselectivity and at low cost.

A further advantage of the present invention is that methylhydrazine can be used in aqueous diluted form, which is less hazardous then using methylhydrazine in substantially pure form. This advantage makes the invention particular useful for large-scale production in agrochemistry.

The present invention is illustrated with the aid of the following Examples:

EXAMPLE P1

Preparation of 3-difluoromethyl-1-methyl-1H-pyrazole-4-carboxylic acid using Process Steps a) and b1) in xylene Process Step a):

300 mmol of methylhydrazine (in the form of a 35% (w/w) aqueous solution) and 60 mmol NaOH (in the form of a 30% (w/w) aqueous solution) are dissolved in 75 g water (total amount of water is 19.7 equivalents relative to the compound of formula II). A solution of 2-[1-Ethoxy-meth-(Z)-ylidene]-4,4-difluoro-3-oxo-butyric acid ethyl ester in 90 g xylene (2.8 equivalents relative to the compound of formula II) is added during 30 minutes at 15° C. The reaction mixture is stirred for 10 minutes at 25° C.

Process Step b1):

450 mmol NaOH (in the form of a 30% (w/w) aqueous solution) is added and the reaction mixture is stirred for 45 minutes at 65° C.

The aqueous phase is isolated from the organic phase at 65° C. and added to a solution of 50 g water and 570 mmol HCl (in the form of a 32% (w/w) solution), which is pre-heated to 95° C. The reaction mixture is stirred for 10 minutes at 95° C. and a precipitate is formed.

Isolation of 3-difluoromethyl-1-methyl-1H-pyrazole-4-carboxylic acid

The suspension is cooled to 25° C. over 3 hours and the precipitate is collected by filtration, washed twice with 75 g water at a temperature of 0° C. and dried at 60° C. under vacuum. 3-Difluoromethyl-1-methyl-1H-pyrazole-4-carboxylic acid is obtained in the form of white crystals (m.p.: 204° C.; yield: 88%; ratio wanted/unwanted isomer: 99.99: 0.01). The "desired isomer" is 3-difluoromethyl-1-methyl-1H-pyrazole-4-carboxylic acid; the "undesired isomer" is 5-difluoromethyl-1-methyl-1H-pyrazole-4-carboxylic acid.

EXAMPLE P2

Preparation of 3-difluoromethyl-1-methyl-1H-pyrazole-4-carboxylic acid using Process Steps a) and b1)

In Example P2, different solvents are tested. Besides using different solvents, all other reaction conditions are as described in Example P1 above. Yields and regioselectivity are measured on the stage of the anion of the compound of formula I being in aqueous solution, i.e. after isolation of the aqueous phase and before adding said aqueous phase to the HCl-solution. For example 2, the amount of base-solution in step a) was replaced by water. For comparative example C1 (no organic solvent) the amount of organic solvent in step a) was replaced by water and the 2-[1-Ethoxy-meth-(Z)-ylidene]-4,4-difluoro-3-oxo-butyric acid ethyl ester was added in pure form. For comparative example C2 the water-miscible organic solvent ethanol was used.

| Example no. | Solvent | Base present in step a) | Yield | ratio desired/ undesired isomer |
|---|---|---|---|---|
| 1 | Xylene | NaOH | 94% | 97:3 |
| 2 | Xylene | — | 84% | 89:11 |
| 3 | Toluene | NaOH | 94% | 97:3 |
| 4 | Chlorbenzene | NaOH | 87% | 95:5 |
| 5 | Methyl-isobutylketone | NaOH | 90% | 97:3 |
| 6 | Cyclohexane | NaOH | 86% | 91:9 |
| 7 | Dioxane | NaOH | 78% | 91:9 |
| C1 | — | NaOH | 75% | 85:15 |
| C2 | Ethanol | NaOH | 74% | 80:20 |

EXAMPLE P3

Preparation of Ethyl 3-difluoromethyl-1-methyl-1H-pyrazole-4-carboxylate Without Base A 0.25 mol solution of methylhydrazine 40% diluted in 50.0 g xylene and 4.7 g water was prepared. A solution of 0.25 mol of 2-[1-Ethoxy-meth-(Z)-ylidene]-4,4-difluoro-3-oxo-butyric acid ethyl ester in 100.0 g xylene was added to the methylhydrazine over 30-60 minutes at a temperature of 20-25° C. The reaction mixture was stirred for 15 min. The phases of the reaction mass were separated.

EXAMPLE P4

Preparation of 3-difluoromethyl-1-methyl-1H-pyrazole-4-carboxylic acid

To the organic phase obtained in P3 19 g water and 0.51 mol NaOH 30% were added and heated to 60-65° C. The reaction mass was stirred during 45 minutes at 60-65° C. The phases of the reaction mixture were separated at 60-65° C. The alkaline water phase (product phase) was added to a solution of 20.0 g water and 0.54 mol of HCl 32% at 80-85° C. The reaction mass was stirred over 5-10 minutes at 80-85° C. The suspension was cooled down from 80-85° C. to 0-5° C. The suspension was filtered off and crystals washed 2× with 42.5 g of water (0° C., displacement-washing). The product was dried at 60° C. under reduced pressure.

Further Examples are shown in the Table below. Except where stated the reactants and conditions are those of Example P3 and P4. The methylhydrazine used was 35% and no extra water was added. The w/w ratio of xylene:methylhydrazine was 60:40 and the w/w ratio of xylene to 2-[1-Ethoxy-meth-(Z)-ylidene]-4,4-difluoro-3-oxo-butyric acid ethyl ester was 63:37.

| Example no. | Temperature | Yield | ratio desired/ undesired isomer |
|---|---|---|---|
| 11 | −15° C. | 83 | 95/5 |
| 12 | 5° C. | 84 | 96/4 |
| 13 | 25° C. | 86 | 95/5 |
| C3 | 60° C. | 76 | 91/9 |

Further Examples are shown in the Table below. Except where stated the reactants and conditions are those of Example P3 and P4.

| Example no. | Mass Ratio Xylene/ MMH 35% | Mass Ratio Xylene/ Formula II | Temp. | Yield | ratio desired/ undesired isomer |
|---|---|---|---|---|---|
| 14 | 60/40 | 63/37 | 10° C. | 87 | 95/5 |
| 15 | 70/30 | 71/29 | 8° C. | 87 | 96/6 |
| 16 | —/100 | 79/21 | 10° C. | 81 | 95/5 |
| 17 | —/100 | 72/28 | 10° C. | 80 | 93/7 |
| 18 | —/100 | 55/45 | 15° C. | | 88/12 |
| 19 | —/100 | —/100 | 15° C. | | 80/20 |

What is claimed is:

1. A process for the production of a compound of formula I

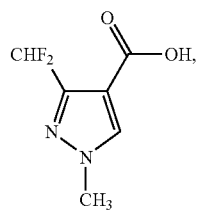

which comprises a) reacting a compound of formula II

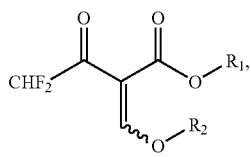

wherein $R_1$ and $R_2$ are both independently $C_1$-$C_6$alkyl, with methylhydrazine in the presence of water and a water-immiscible organic solvent being inert in saponification reactions, to form a compound of formula III

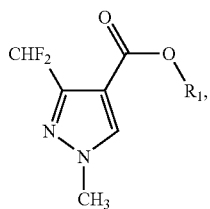

wherein $R_1$ is as defined for formula I; and b) saponifying that compound in situ leading to the formation of the compound of formula I by b1) adding a base to form the anion of the compound of formula I and then adding an acid to form the compound of formula I; or b2) adding an acid to form the compound of formula I.

2. A process according to claim 1, wherein $R_1$ and $R_2$ are both ethyl.

3. A process according to claim 1, wherein the organic solvent is an optionally halogenated aromatic hydrocarbon solvent, a ketone solvent, an optionally halogenated hydrocarbon solvent or an ether solvent.

4. A process according to claim 3, wherein the organic solvent is an aromatic hydrocarbon solvent.

5. A process according to claim 4, wherein the organic solvent is xylene.

6. A process according to claim 1, wherein the compound of formula III is saponified by b1) adding a base to form the anion of the compound of formula I and then adding an acid to form the compound of formula I.

7. A process according to claim 6, wherein the aqueous phase is isolated before the addition of the acid.

8. A process according to claim 6, wherein step a) is carried out at a reaction temperature of from −20° C. to 50° C. and step b1) is carried out at a reaction temperature of 50° C. to 100° C.

9. A process according to claim 1, wherein the compound of formula III is saponified by b2) adding an acid to form the compound of formula I.

10. A process according to claim 9, wherein the acid is used in the amount of at least 0.01 equivalents relative to compounds of formula II used in step a).

11. A process according to claim 9, wherein the organic phase is isolated before the acid is added and wherein the acid is added to said organic phase.

12. A process according to claim 11, wherein step a) is carried out at a reaction temperature of from −20° C. to 50° C. and step b2) is carried out at a reaction temperature of 50° C. to 100° C.

13. A process according to claim 1 wherein in step a) no base is added.

14. A process according to claim 13, wherein step a) is carried out using a molar ratio of methylhydrazine :compound of formula II of from 1:0.8 to 1:1.2.

15. A process according to claim 14, wherein step a) is carried out at a reaction temperature of from −20° C. to 50° C.

16. A process according to claim 15, wherein step a) is carried out using a ratio of compound of methylhydrazine to organic solvent of from 1:1 to 1:20.

17. A process according to claim 1 wherein in step a) a base is present.

18. A process according to claim 17, wherein in process step a) at least one equivalent of water is added at the start of the reaction relative to compounds of formula II.

19. A process according to claim 18, wherein the molar ratio between the water added at the start of the reaction and the organic solvent is from 20:1 to 1:20.

20. A process according to claim 17, wherein in step a) a hydroxide is present and wherein the compound of formula III is saponified by b1) adding a hydroxide base to form the anion of the compound of formula I and then adding an acid to form the compound of formula I.

21. A process according to claim 20, wherein in step a) the hydroxide base is present in an amount of 0.1 to 0.5 equivalents relative to the compounds of formula II; and in step b1) the hydroxide base is added so that a total amount of hydroxide base is present in an amount of at least 1 equivalent relative to the amount of compounds of formula II used.

22. A process for the production of a compound of formula III

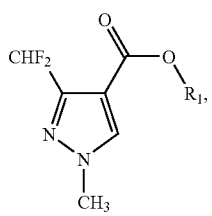
(III)

wherein $R_1$ is $C_1$-$C_6$alkyl which comprises reacting a compound of formula II

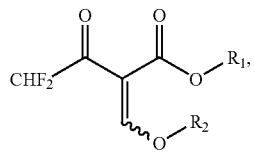
(II)

wherein $R_1$ and $R_2$ are both independently $C_1$-$C_6$alkyl, with methylhydrazine in the presence of water and a water-immiscible organic solvent in the absence of a base.

* * * * *